United States Patent [19]

Knops et al.

[11] 4,451,282
[45] May 29, 1984

[54] HERBICIDALLY ACTIVE NOVEL HETERO-SUBSTITUTED PYRID-4-ONE DERIVATIVES

[75] Inventors: Hans-Joachim Knops; Peter Babczinski, both of Wuppertal; Ludwig Eue, Leverkusen; Robert Schmidt, Bergisch-Gladbach, all of Fed. Rep. of Germany

[73] Assignee: Bayer Aktiengesellschaft, Leverkusen, Fed. Rep. of Germany

[21] Appl. No.: 411,749

[22] Filed: Aug. 26, 1982

[30] Foreign Application Priority Data

Sep. 5, 1981 [DE] Fed. Rep. of Germany ....... 3135186

[51] Int. Cl.³ .................... A01N 43/40; C07D 401/02
[52] U.S. Cl. ....................................... 71/92; 546/276; 546/278; 546/279
[58] Field of Search ....................... 546/276, 278, 279; 71/92, 93

[56] References Cited

U.S. PATENT DOCUMENTS 4,152,136 5/1979 Taylor ...................................... 71/90
4,235,619 11/1980 Taylor ...................................... 71/66

*Primary Examiner*—Jane T. Fan

*Attorney, Agent, or Firm*—Sprung, Horn, Kramer & Woods

[57] ABSTRACT

Hetero-substituted pyrid-4-one derivatives of the general formula

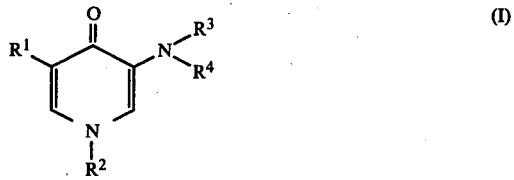

(I)

in which
  $R^1$ represents an optionally substituted phenyl radical,
  $R^2$ represents an alkyl, alkenyl, alkinyl, alkoxy, alkoxyalkyl or dialkylamino radical, and
  $R^3$ and $R^4$, together with the nitrogen atom to which they are bonded, represent an optionally substituted heterocyclic radical, are novel, are produced as described and find use as herbicides, especially as selective herbicides for combating graminaceous weeds in crops such as cotton, wheat, soy beans and corn.

9 Claims, No Drawings

HERBICIDALLY ACTIVE NOVEL HETERO-SUBSTITUTED PYRID-4-ONE DERIVATIVES

The present invention relates to certain new hetero-substituted pyrid-4-one derivatives, to a process for their production and their use as herbicides, in particular as selective herbicides.

It has already been disclosed that 3,5-disubstituted pyrid-4-ones, such as 1-methyl-3-phenyl-5-(3-trifluoromethylphenyl)-pyrid-4-one, can be employed as herbicides, in particular also for selectively combating weeds in cotton (see U.S. Pat. Nos. 4,152,136 and 4,235,619).

However, they can be used selectively in various other crop plants only to a limited extent, since damage to these plants can occur.

The present invention now provides, as new compounds, the hetero-substituted pyrid-4-one derivatives of the general formula

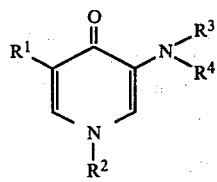

in which
R$^1$ represents an optionally substituted phenyl radical,
R$^2$ represents an alkyl, alkenyl, alkinyl, alkoxy, alkoxyalkyl or dialkylamino radical, and
R$^3$ and R$^4$, together with the nitrogen atom to which they are bonded, represent an optionally substituted heterocyclic radical.

According to the present invention there is further provided a process for the production of a compound of the present invention characterized in that a ketone of the general formula

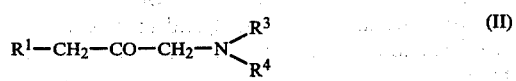

in which R$^1$, R$^3$ and R$^4$ have the meanings given above, is first reacted with a formylating agent in the presence of a base and in the presence of a diluent, and thereafter with a salt of an amine of the general formula

R$^2$—NH$_2$     (III)

in which R$^2$ has the meaning given above, is added, in the presence of the same diluent, and the mixture of the two resulting enamines of the general formulae

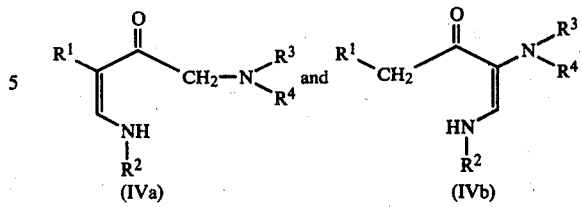

in which R$^1$, R$^2$, R$^3$ and R$^4$ have the meanings given above, is subjected, without isolation, to the same reaction sequence - reaction with the same formylating agent and with the same amine salt under the same reaction conditions.

The new hetero-substituted pyrid-4-one derivatives of the formula (I) possess good herbicidal properties, in particular selective herbicidal properties. The active compounds according to the present invention thus represent an enrichment of herbicidal agents, in particular of the selective chemical combating of weeds.

Preferred compounds of formula (I) according to the present invention are those in which R$^1$ represents a phenyl radical which is optionally monosubstituted or polysubstituted by identical or different substituents (preferred substituents being selected from halogen, alkyl, alkoxy or alkylthio, each having 1 to 4 carbon atoms, and halogenoalkyl having 1 or 2 carbon atoms and 1 to 5 identical or different halogen atoms - preferably, fluorine atoms and chlorine atoms);

R$^2$ represents an alkyl radical having 1 to 4 carbon atoms, an alkenyl or alkinyl radical, each having 3 to 4 carbon atoms, an alkoxy or alkoxyalkyl radical, each having 1 to 4 carbon atoms in each alkyl part, or a dialkylamino radical having 1 to 4 carbon atoms in each alkyl part; and R$^3$ and R$^4$, together with the nitrogen atom to which they are bonded, represent a 5-membered heterocyclic radical which is optionally substituted by alkyl or alkoxy, each having 1 to 4 carbon atoms, or by halogen, and contains 1 to 3 nitrogen atoms.

Particularly preferred compounds of the formula (I) according to the present invention are those in which R$^1$ represents a phenyl radical which is optionally monosubstituted or disubstituted by identical or different substituents selected from fluorine, chlorine, bromine, methyl, ethyl, isopropyl, methoxy, ethoxy, isopropoxy, methylthio, ethylthio, isopropylthio and trifluormethyl;

R$^2$ represents a methyl, ethyl, i-propyl, allyl, propargyl, methoxy, ethoxy, methoxymethyl, ethoxymethyl, ethoxyethyl or dimethylamino radical, and R$^3$ and R$^4$, together with the nitrogen atom to which they are bonded, represent a heterocyclic radical which is optionally substituted by methyl, methoxy or chlorine and is selected from 1,2,4-triazolyl, imidazolyl and pyrazolyl.

If, for example, 1-(3-trifluoromethylphenyl)-3-(1,2,4-triazol-1-yl)-propanone is used as the starting material, ethyl formate as the formylating agent, and methylamine hydrochloride as the amine component, the course of the reaction according to the present invention is illustrated by the following equation:

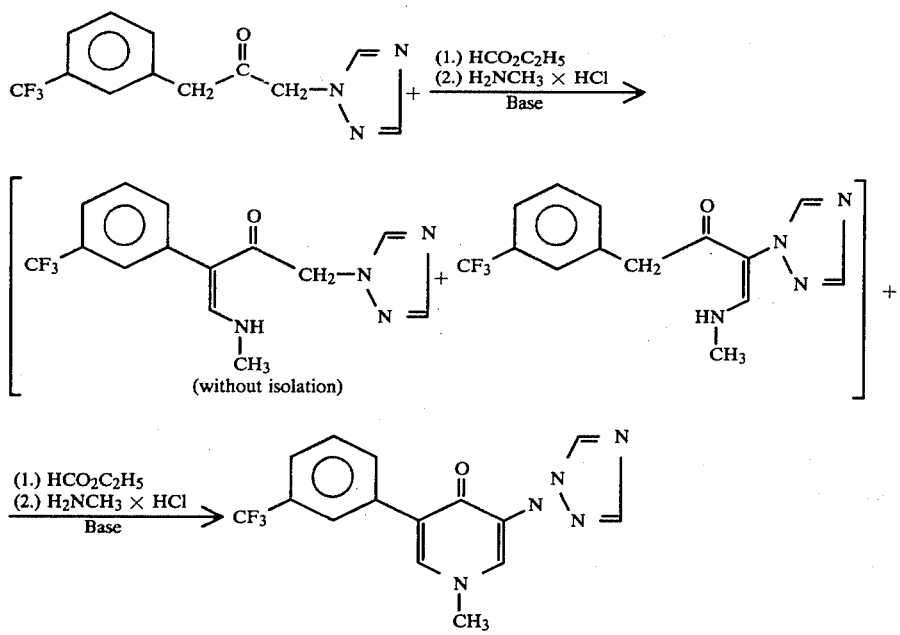

Preferred ketones of formula (II) to be used as starting materials for the reaction according to the invention are those in which $R^1$, $R^3$ and $R^4$ represent the radicals which have already been mentioned for these substituents in connection with the description of the preferred and particularly preferred compounds of formula (I) according to the present invention.

Ketones of the formula (II) are known, and can be obtained in a known manner by reacting, for example, a benzyl cyanide of the general formula $$R^1-CH_2-CN \qquad (IV)$$

in which $R^1$ has the meaning given above, with an acetic acid ester derivative of the general formula $$RO-CO-CH_2NR^3R^4 \qquad (V)$$

in which
R represents an alkyl radical having 1 to 4 carbon atoms and
$R^3$ and $R^4$ have the meanings given above,
in the presence of a base (such as sodium ethylate) and in the presence of an inert organic solvent (such as ethanol), preferably at the boiling point of the solvent used, and then effecting hydrolysis in the system sulphuric acid/water (see also the preparative examples hereinbelow). The benzyl cyanides of the formula (IV) and the acetic acid ester derivatives of the formula (V) are generally known compounds of organic chemistry and can be prepared in a customary manner.

Any of the formylating reagents which can customarily be used can be employed as the formylating agent for the reaction according to the invention. These include, as preference, formic acid esters (such as methyl formate and ethyl formate).

Preferred amines of formula (III) additionally to be used as starting materials for the reaction according to the invention are those in which $R^2$ represents the radicals which have already been mentioned for this substituent in connection with the description of the preferred and particularly preferred compounds of formula (I) according to the present invention. The amines of the formula (III) are employed in the form of their salts, for example as hydrohalides or hydrosulphates. The amines of the formula (III) are generally known compounds of organic chemistry.

The reaction according to the invention is carried out in the presence of a base. Any of the organic and inorganic bases which can customarily be used can be employed for this purpose, such as, in particular, alcoholates (for example, sodium methylate or ethylate and potassium tert.-butylate), sodium hydride or potassium hydride.

Water-miscible organic solvents are preferred diluents for the reaction according to the invention. These preferably include ethers, such as, in particular, tetrahydrofuran or dioxane. In carrying out the process according to the invention, the reaction temperatures can be varied within a certain range. In general, the reaction is carried out at a temperature between $-20°$ and $+60°$ C., preferably at a temperature between $-10°$ and $40°$ C.

In carrying out the process according to the invention, an excess of formylating agent, in particular two to three times the amount, an excess of base, in particular two to three times the amount, and an excess of amine of the formula (III), in particular also two to three times the amount, are first employed per mol of the ketone of the formula (II). The same excess amounts of formylating agent, base and amine are employed when the reaction sequence according to the invention is repeated (ring closure reaction). The working-up and isolation of the end products of the formula (I) are effected in a generally customary manner.

The active compounds according to the invention influence plant growth and can therefore be used as defoliants, desiccants, agents for destroying broad-leaved plants, germination inhibitors and, especially, as weedkillers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annula cultures.

The active compounds according to the invention are well tolerated by productive plants, in addition to showing a very good herbicidal action. Thus, it is possible selectively to combat important graminaceous weeds in important crop plants, such as in cotton, wheat, soy beans and corn.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite wast liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixing being possible. Mixtures with other known active compounds, such as fungicides, insecticides, acaricides, nematicides, bird repellents, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering or dusting.

The active compounds according to the invention can be applied either before or after emergence of the plants. They are preferably applied before emergence of the plants, that is to say by the pre-emergence method. They can also be incorporated into the soil before sowing.

The amount of active compound used can vary within a substantial range. It depends essentially on the nature of the desired effect. In general, the amounts used are between 0.1 and 10 kg of active compound per ha, preferably between 0.1 and 5 kg/ha.

The present invention also provides herbicidal composition containing as active ingredient a compound of the present invention in admixture with a solid diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a dliuent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The examples which follow serve to illustrate the invention.

PREPARATIVE EXAMPLES

Example 1

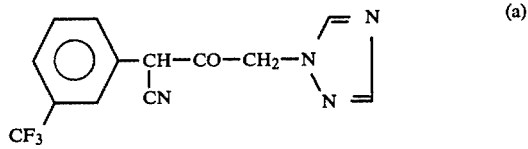
(a)

128 g of ethyl 1,2,4-triazolylacetate and 123.3 g of 3-trifluoromethylbenzyl cyanide were added dropwise to a boiling solution of 30.6 g of sodium in 500 ml of ethanol in the course of 6 hours, and the mixture was then heated under reflux for 12 hours. The precipitate which separated out after the mixture had cooled was dissolved in water, and the solution was extracted with ether to remove unreacted educts. The aqueous phase was acidified to pH 3 with dilute hydrochloric acid, the precipitate was filtered off under suction, the filtrate was extracted with ether, and the extract was dried and concentrated. The precipitates were combined. 266 g of 1-cyano-1-(3-trifluoromethylphenyl)-3-(1,2,4-triazol-1-yl)-propanone hydrochloride of melting point 95° to 98° C. were obtained.

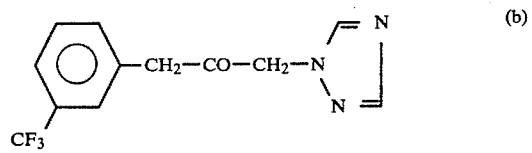
(b)

320 ml of concentrated sulphuric acid and 94 ml of water were added to 266.3 g of 1-cyano-1-(3-trifluoromethylphenyl)-3-(1,2,4-triazol-1-yl)-propanone hydrochloride, and the mixture was heated at 100° C. for 1.5 hours. After the vigorous evolution of $CO_2$ had ended, the mixture was allowed to cool, and 940 ml of water were added. After a short time at from 0° to 20° C., the sulphate of the desired end product crystallized out. This was suspended in water, and the suspension was adjusted to a pH value of 7-8 with sodium bicarbonate solution. The resulting crystalline precipitate was filtered off under suction, dissolved in chloroform, dried over sodium sulphate and concentrated. 131.3 g (72% of theory) of 1-(3-trifluoromethylphenyl)-3-(1,2,4-triazol-1-yl)-propanone of melting point 85° to 87° C. were obtained.

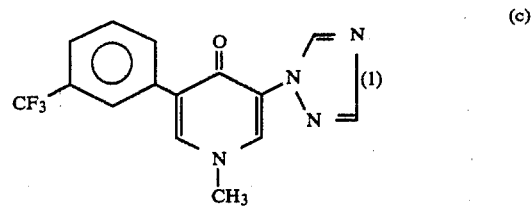
(c)

27 g of 1-(3-trifluoromethylphenyl)-3-(1,2,4-triazol-1-yl)-propanone in 100 ml of tetrahydrofuran were added dropwise to 7.8 g of 80% strength sodium hydride in 100 ml of absolute tetrahydrofuran at −5° C. to 0° C. 20.3 ml of ethyl formate were added to this reaction solution at the same temperature. After a further hour, 16.5 ml of ethyl formate were again added. The mixture was allowed to warm up to room temperature, and was stirred overnight. Thereafter, 16.8 g of methylamine hydrochloride in 50 ml of water were added, the temperature increasing to 30° C. The reaction mixture was kept at this temperature for half an hour. After the mixture had cooled, 200 ml of methylene chloride and 100 ml of water were added to the filtered solution, and the organic phase was separated off, washed again with water, dried over sodium sulphate and concentrated. The residue, a mixture of the two enamines, was again subjected to the same reaction. Ether was added to the residue then obtained, and the crystalline precipitate was filtered off under suction. 8 g (25% of theory) of 1-methyl-3-(1,2,4-triazol-1-yl)-5-(3-trifluoromethylphenyl)-pyrid-4-one of melting point 181° to 183° C. were obtained.

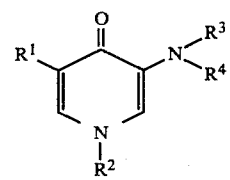

which are listed in Table 2 below were also obtained in a corresponding manner:

TABLE 2

| Compound No. | $R^1$ | $R^2$ | $-NR^3R^4$ | Melting point (°C.) |
|---|---|---|---|---|
| 2 | ⌬-CF3 | —OCH3 | ⌬triazolyl | 262–270 |
| 3 | ⌬-CF3 | —N(CH3)2 | ⌬triazolyl | 147–149 |

TABLE 2-continued

| Compound No. | R¹ | R² | —NR³R⁴ | Melting point (°C.) |
|---|---|---|---|---|
| 4 | 3-CF₃-C₆H₄ | —CH₂CH=CH₂ | 1,2,4-triazol-1-yl | 96–102 |
| 5 | 3-CF₃-C₆H₄ | —CH₂CH₂OCH₃ | 1,2,4-triazol-1-yl | Oil |
| 6 | 3-CF₃-C₆H₄ | —C₂H₅ | 1,2,4-triazol-1-yl | 171–172 |
| 7 | 3-CF₃-C₆H₄ | n-C₃H₇ | 1,2,4-triazol-1-yl | 109–110 |
| 8 | 3-CF₃-C₆H₄ | i-C₃H₇ | 1,2,4-triazol-1-yl | 134–135 |
| 9 | 3-CF₃-C₆H₄ | —CH₃ | 1,2,4-triazol-1-yl | 97 |
| 10 | 3-CF₃-C₆H₄ | —CH₃ | 3-Cl-1,2,4-triazol-1-yl | 164–165 |
| 11 | 3-Cl-5-CF₃-C₆H₃ | —CH₃ | 1,2,4-triazol-1-yl | 189–190 |
| 12 | 3-CF₃-C₆H₄ | —CH₃ | 3,5-dimethylpyrazol-1-yl | |

The herbicidal activity of the compounds of this invention is illustrated by the following biotest example.

In this example, the compound according to Example 1 of the present invention is identified by the number (1).

Example 2
Pre-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was rated in % damage in comparison to the development of the untreated control. The figures denoted:

0%=no action (like untreated control)
100%=total destruction

In this test, for example, the compound (1), in addition to showing a very good general herbicidal action, was well tolerated by productive plants, such as corn, soy beans, wheat and cotton. It will be appreciated that the instant specification and examples are set forth by way of illustration and not limitation, and that various modifications and changes may be made without departing from the spirit and scope of the present invention.

We claim:

1. A hetero-substituted pyrid-4-one derivative of the formula

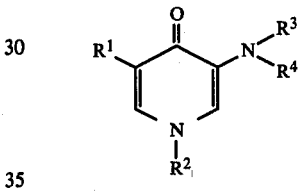

in which
R¹ represents a phenyl radical which is optionally monosubstituted or polysubstituted by identical or different substituents selected from halogen, alkyl, alkoxy or alkylthio, each having 1 to 4 carbon atoms, and halogenoalkyl having 1 or 2 carbon atoms and 1 to 5 identical or different halogen atoms,
R² represents an alkyl having 1 to 4 carbon atoms, an alkenyl or alkinyl radical, each having 3 to 4 carbon atoms, an alkoxy or alkoxyalkyl radical, each having 1 to 4 carbon atoms in each alkyl part, or a dialkylamino radical having 1 to 4 carbon atoms in each alkyl part, and
R³ and R⁴, together with the nitrogen atom to which they are bonded, represent a heterocyclic radical which is optionally substituted by methyl, methoxy or chlorine and is selected from 1,2,4-triazolyl, imidazolyl and pyrazolyl.

2. A compound according to claim 1, in which
R¹ represents a phenyl radical which is optionally monosubstituted or disubstituted by identical or different substituents selected from fluorine, chlorine, bromine, methyl, ethyl, isopropyl, methoxy, ethoxy, isopropoxy, methylthio, ethylthio, isopropylthio and trifluoromethyl; and
R² represents a methyl, ethyl, i-propyl, allyl, propargyl, methoxy, ethoxy, methoxymethyl, ethoxymethyl, ethoxyethyl or dimethylamino radical.

3. A compound according to claim 1, wherein such compound is 1-methyl-3-(1,2,4-triazol-1-yl)-5-(3-trifluoromethylphenyl)-pyrid-4-one of the formula

4. A compound according to claim 1, wherein such compound is 1-methyl-3-(pyrazol-1-yl)-5-(3-trifluoromethyl-phenyl)-pyrid-4-one of the formula

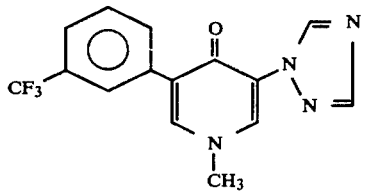

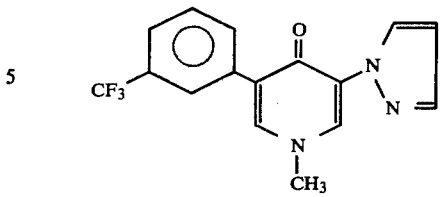

5. A herbicidal composition comprising a herbicidally effective amount of a compound according to claim 1, in admixture with a diluent.

6. A composition according to claim 5, characterized in that it contains from 0.1 to 95% of the active compound, by weight.

7. A method of combating weeds, comprising applying to the weeds, or to a habitat thereof, a herbicidally effective amount of a compound according to claim 1.

8. A method of combating weeds in the growing of a cotton, wheat, soy bean or corn crop comprising applying to the weeds or to the field in which the crop is being grown a herbicidally effective amount of a compound according to claim 3.

9. A method of combating weeds in the growing of a cotton, wheat, soy bean or corn crop comprising applying to the weeds or to the field in which the crop is being grown a herbicidally effective amount of a compound according to claim 4.

* * * * *

UNITED STATES PATENT AND TRADEMARK OFFICE
CERTIFICATE OF CORRECTION

PATENT NO. : 4,451,282
DATED : May 29, 1984
INVENTOR(S) : Hans-Joachim Knops, et al It is certified that error appears in the above-identified patent and that said Letters Patent is hereby corrected as shown below:

Col. 4, end of 3rd formula  Delete 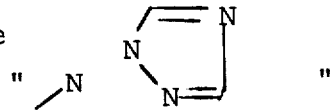

and substitute

Col. 5, line 45  Delete "annula" and substitute --annual--

Signed and Sealed this

Twenty-fifth Day of December 1984

[SEAL]

Attest:

Attesting Officer

GERALD J. MOSSINGHOFF

*Commissioner of Patents and Trademarks*